United States Patent [19]
Anderskewitz et al.

[11] Patent Number: 6,133,479
[45] Date of Patent: Oct. 17, 2000

[54] PHENYLETHYLAMINE DERIVATIVES, PROCESSES FOR PREPARING THEM AND THEIR USE AS PHARMACEUTICAL COMPOSITIONS

[75] Inventors: Ralf Anderskewitz, Bingen; Franz Birke, Ingelheim am Rhein; Hans M. Jennewein, Wiesbaden, all of Germany

[73] Assignee: Boehringer Ingelheim Pharma KG, Ingelheim, Germany

[21] Appl. No.: 09/363,864

[22] Filed: Jul. 29, 1999

[30] Foreign Application Priority Data

Jul. 31, 1998 [DE] Germany .............................. 198 34 713

[51] Int. Cl.[7] .......................... C07C 213/00; A01N 33/02
[52] U.S. Cl. .............................................. 564/347; 514/648
[58] Field of Search ................................ 564/347; 514/648

[56] References Cited

FOREIGN PATENT DOCUMENTS 19834713   2/2000   Germany .

9849131   11/1998   WIPO .

Primary Examiner—Paul J. Killos
Attorney, Agent, or Firm—Robert P. Raymond; Alan R. Stempel; Mary-Ellen M. Devlin

[57] ABSTRACT

The present invention relates to new phenylethylamine derivatives, processes for preparing them and their use as pharmaceutical compositions. The phenylethylamines according to the invention correspond to the general formula:

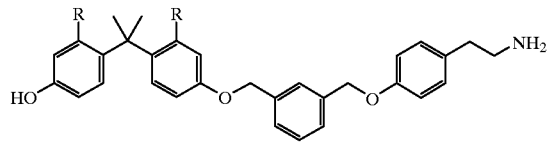

10 Claims, No Drawings

PHENYLETHYLAMINE DERIVATIVES, PROCESSES FOR PREPARING THEM AND THEIR USE AS PHARMACEUTICAL COMPOSITIONS

The present invention relates to new phenylethylamine derivatives, processes for preparing them and their use as pharmaceutical compositions. The phenylethylamine derivatives according to the invention correspond to general formula 1

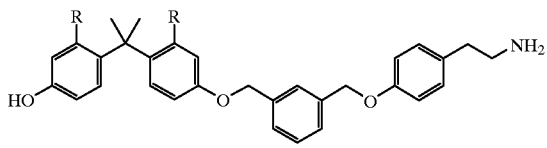

wherein
R independently of one another may denote hydrogen or fluorine
in the form of the free bases or the corresponding acid addition salts with pharmacologically acceptable acids.

The following two compounds are preferred:

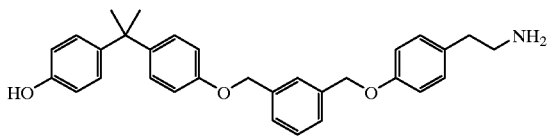

and

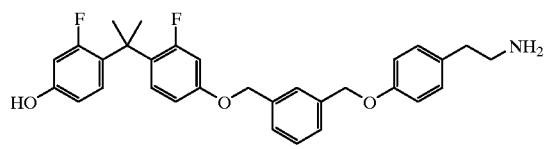

As has been found, the compounds of formula 1 according to the invention are characterised by their versatility in the therapeutic field and by their efficacy when taken orally. Particular emphasis should be placed on the possible applications in which the $LTB_4$-receptor-antagonistic properties play a part. The following are worthy of special mention:

Arthritis, asthma, chronic obstructive lung diseases, e.g. chronic bronchitis, $\alpha_1$-antitrypsin deficiency, psoriasis, ulcerative colitis, inflammatory bowel disorders, gastropathy or enteropathy induced by nonsteroidal antiinflammatories, cystic fibrosis, Alzheimer's disease, shock, reperfusion damage/ischaemia, atherosclerosis, multiple sclerosis.

The new compounds may also be used to treat diseases or conditions in which the passage of cells from the blood through the vascular system and into the tissues is of importance (e.g. metastasis) or diseases and conditions in which the combination of the $LTB_4$ or another molecule (such as 12-HETE) with the $LTB_4$ receptor has an influence on cell proliferation (such as chronic myeloid leukaemia). The new compounds may also be used in conjunction with other active substances, e.g. those which are used for the same indications, or for example with antiallergics, secretolytics, $\beta_2$-adrenergics, steroids for inhalation and oral administration, antihistamines, PAF antagonists, NSAID and glucocorticoids. The compositions may be administered topically, orally, transdermally, nasally, parenterally or by inhalation.

The activity may be investigated pharmacologically and biochemically using tests as described, for example, in WO 93/16036, pp. 15–17 ("Mouse ear test"), to which reference is hereby made.

The compounds according to the invention have proved to be particularly highly potent $LTB_4$ antagonists both in vitro and in vivo. The two substances according to the invention exhibit high-affinity binding to the $LTB_4$ receptor. In addition, when administered orally, they have $ED_{50}$ values of 0.02 and 0.03 mg/kg in the mouse ear test mentioned above.

The therapeutic or prophylactic dose depends, not only on the potency of the individual compounds and the body weight of the patient, but also on the nature and gravity of the illness. For oral use the dose is between 1 and 500 mg, preferably between 20 and 250 mg. By inhalation the patient is given between about 0.5 and 25 mg, preferably between about 2 and 20 mg of active substance.

Solutions for inhalation generally contain between about 0.5 and 5% of active substance. The new compounds may be administered in conventional preparations, e.g. as plain or coated tablets, capsules, lozenges, powders, granules, solutions, emulsions, syrups, aerosols for inhalation, ointments and suppositories.

The Examples which follow show some possible formulations for the preparations:

EXAMPLES OF FORMULATIONS

1. Tablets a) Prepared by Pluronic melt incorporation

| Content | 1% | 10% |
|---|---|---|
| Active substance of formula 1 | 1 mg | 10 mg |
| Poloxamer NF | 99 mg | 90 mg | b) Wettability improved formulation

| Content | 25 mg | 75 mg |
|---|---|---|
| Active substance of formula 1 | 25 mg | 75 mg |
| Microcrystalline cellulose | 22.75 mg | 68.25 mg |
| Lactose monohydrate | 22.75 mg | 68.25 mg |
| Methylcellulose | 1.25 mg | 3.75 mg |
| Sodium laurylsulphate | 0.25 mg | 0.75 mg |
| Crospovidone(s) | 2.25 mg | 6.75 mg |
| Magnesium stearate | 0.75 mg | 2.25 mg |
| Total | 0.75 mg | 225 mg |

2. Suppositories

| Composition | |
|---|---|
| Active substance according to the invention | 100 parts by weight |
| Powdered lactose | 45 parts by weight |
| Cocoa butter | 1555 parts by weight |

The ingredients are processed in the usual way to form suppositories weighing 1.7 g.

3. Powder for inhalation

Micronised powdered active substance (compound of formula 1; particle size approximately 0.5 to 7 $\mu$m) is packed into hard gelatine capsules in an amount of 5 mg, optionally with the addition of micronised lactose. The powder is inhaled using conventional inhalers, e.g. according to DE-A 33 45 722, to which reference is hereby made.

The new compounds may be prepared by methods known from the prior art. The following three methods are particularly advantageous:

1. Reacting the protected phenol of general formula 2

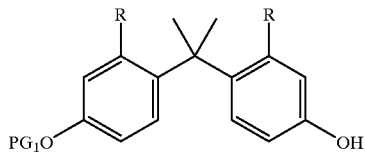
(2)

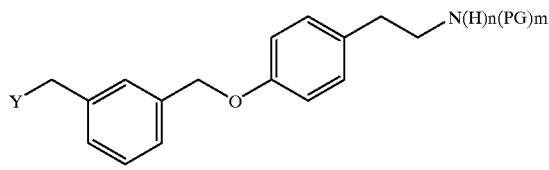
(3)

with an ethylamine derivative of general formula 3 wherein $PG_1$ may denote a protecting group suitable for protecting phenols or else denotes hydrogen;

PG may denote a (protecting group) suitable for protecting amines, where n is 0 or 1 and m may denote the integer 1 or 2;

Y may denote fluorine, chlorine, bromine or iodine or a $C_{1-4}$-alkyl or an arylsulphonate group.

The compounds are reacted with basic excipients such as e.g. alkali or alkaline earth metal hydroxides, alkali or alkaline earth metal carbonates, $C_{1-4}$-alkali metal alkoxides in solvents which are inert under the reaction conditions chosen, such as formamides, preferably dimethylformamide (DMF), $C_{1-4}$-alkylnitriles, preferably acetonitrile, $C_{1-4}$-alkyl esters of carboxylic acids, preferably ethyl acetate or ethyl formate, aromatic or aliphatic hydrocarbons, preferably toluene, or in branched or unbranched $C_{1-4}$-alcohols.

In the following reaction step the protecting groups are cleaved, particularly with inorganic or organic acids in suitable solvents or by hydrogenolysis or by other methods known from the prior art which are normally used to cleave specific protecting groups.

2. Reacting two compounds of general formulae 4 and 5:

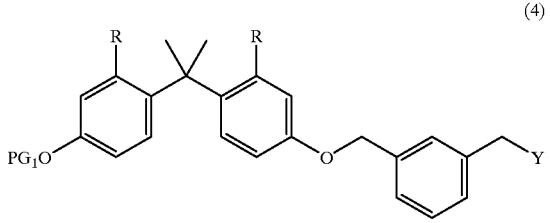
(4)

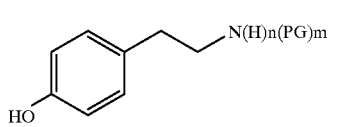
(5)

wherein
$PG_1$ may denote hydrogen or a protecting group suitable for protecting phenols;

PG may denote a protecting group suitable for protecting amines, where n is 0 or 1 and m may denote the integer 1 or 2;

Y may denote fluorine, chlorine, bromine or iodine or a $C_{1-4}$-alkyl or an arylsulphonate group.

The compounds are reacted with basic adjuvants such as e.g. alkali or alkaline earth metal hydroxides, alkali or alkaline earth metal carbonates, $C_{1-4}$-alkali metal alkoxides in solvents which are inert under the reaction conditions chosen, such as formamides, preferably dimethylformamide (DMF), $C_{1-4}$-alkylnitriles, preferably acetonitrile, $C_{1-4}$-alkyl esters of carboxylic acids, preferably ethyl acetate or ethyl formate, aromatic or aliphatic hydrocarbons, preferably toluene, or in branched or unbranched $C_{1-4}$-alcohols.

In the following reaction step the protecting groups are cleaved, particularly with inorganic or organic acids in suitable solvents or by hydrogenolysis or by other methods known from the prior art which are normally used to cleave specific protecting groups.

3. Reduction of the nitrostyrene (6)

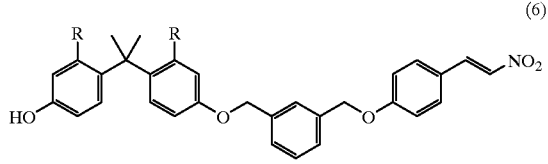
(6)

The compounds according to the invention may be prepared by reduction of the nitrostyrene (6) by heterogeneous or homogeneous hydrogenation using suitable catalysts, using complex hydrides or with boranes in suitable solvents.

Thus, the reduction may be carried out, for example, in a solvent selected from the group comprising methanol, ethanol or a higher alcohol, DMF or water in the presence of a catalyst from the group comprising Raney nickel, Pd/C, platinum or with hydride reagents, particularly complex hydrides from the group comprising $NaBH_4$, $Ca(BH_4)$, $LiAlH_4$ or other aluminium or boron hydrides, at temperatures in the range from 0 to 100° C. and under a hydrogen pressure of at least 760 Torr to yield the corresponding amine of general formula 1.

The protecting groups mentioned in the above description of the production processes and the conditions of the process which have to be adhered to in order to protect the phenolic hydroxyl groups or the secondary or primary amines and subsequently remove them are sufficiently well known from the prior art [T. W. Greene, P. G. Wuts, Protective Groups in Organic Synthesis, $2^{nd}$ edition, Wiley, J/VCH, New York 1991].

Similarly, the conditions for the reduction of the nitro compounds and the reduction agents required for this purpose are sufficiently well known from the prior art [J. March, Jerry: Advanced Organic Chemistry, Reactions, Mechanisms and Structure, $4^{th}$ edition, Wiley New York 1992 and cit. lit.].

Various other embodiments of the processes will be apparent to the skilled person from the present specification. However, it is expressly pointed out that these Examples and the associated description are provided solely as an illustration and are not to be regarded as restricting the invention.

EXAMPLE OF SYNTHESIS

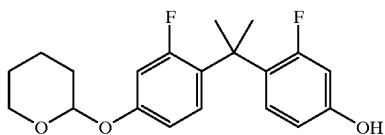
(7)

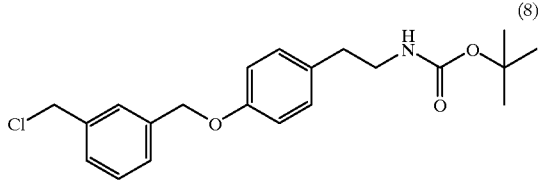
(8)

3.8 g of the THP-protected ether 7, 2.7 g of the BOC-protected amine 8 and 1.5 g of potassium carbonate ($K_2CO_3$) are refluxed in 100 ml of acetonitrile over a period of 5 hours. Then the reaction medium/solvent is distilled off. The residue is divided between water and ethyl acetate. The organic phase is separated off and dried over sodium sulphate ($Na_2SO_4$). After the drying agent has been filtered off the solvent is evaporated down and the residue is purified by chromatography over silica gel with toluene/acetone 95:5. Yield: 2.3 g.

The product is dissolved in 20 ml of ethyl acetate and 10 ml of a 3 M solution of HCl in ethyl acetate and stirred for 12 hours at ambient temperature. The crystals precipitated are dissolved in a little methanol, and the product is precipitated with ether. After suction filtering and drying, 1 g of compound (1) is obtained, R=F,

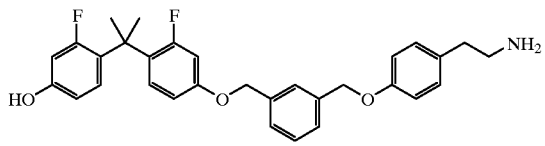

Melting point 173° C.

The compound (1) wherein R=H is prepared analogously, melting point 182–185° C.

What is claimed is:

1. Phenylethylamine derivatives corresponding to general formula 1

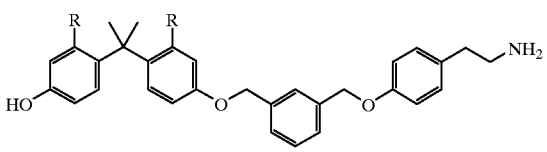
(1)

wherein

R independently of one another may denote hydrogen or fluorine in the form of the free bases or the corresponding acid addition salts with pharmacologically acceptable acids.

2. Phenylethylamine derivatives according to claim 1 of the formula

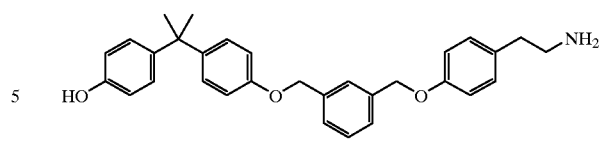

in the form of the free bases or the corresponding acid addition salts with pharmacologically acceptable acids.

3. Phenylethylamine derivative according to claim 1 of the formula

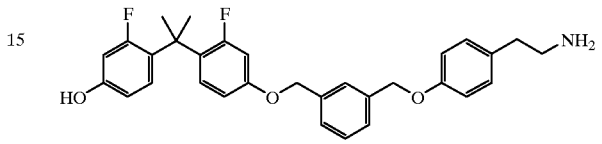

in the form of the free bases or the corresponding acid addition salts with pharmacologically acceptable acids.

4. Process for preparing compounds of general formula 1, characterised in that a compound of formula (2)

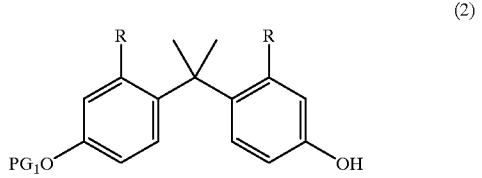
(2)

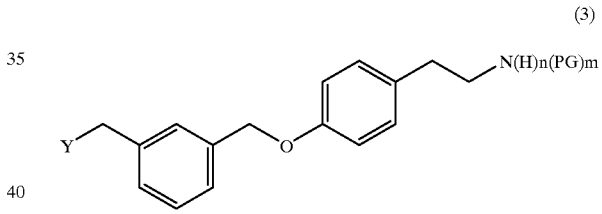
(3)

is reacted with an ethylamine derivative of general formula 3 wherein $PG_1$ may denote a protecting group suitable for protecting phenols, or hydrogen;

PG may denote a protecting group suitable for protecting amines, where n is 0 or 1 and m may denote the integer 1 or 2;

Y may denote fluorine, chlorine, bromine or iodine or a $C_{1-4}$-alkyl or an arylsulphonate group, in the presence of an auxiliary base selected from the group comprising alkali or alkaline earth metal hydroxides, alkali or alkaline earth metal carbonates, $C_{1-4}$-alkali metal alkoxides in solvents which are inert under the reaction conditions chosen, such as formamides, preferably dimethylformamide (DMF), $C_{1-4}$-alkylnitriles, preferably acetonitrile, $C_{1-4}$-alkyl esters of carboxylic acids, preferably ethyl acetate or ethyl formate, aromatic or aliphatic hydrocarbons, preferably toluene, or in branched or unbranched $C_{1-4}$-alcohols, in the following reaction step the protecting groups are cleaved using other methods known from the prior art and the reaction product is isolated.

5. Process for preparing compounds of general formula 1, characterised in that a compound of general formula 4 is reacted with a compound of formula 5

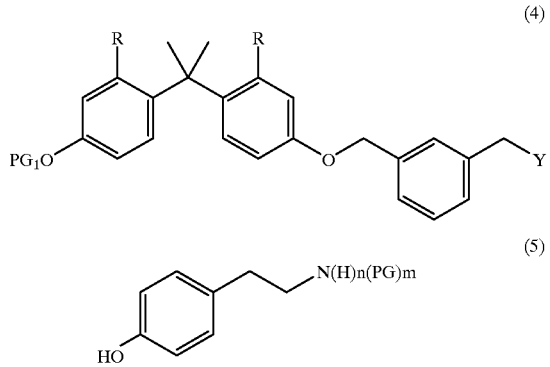

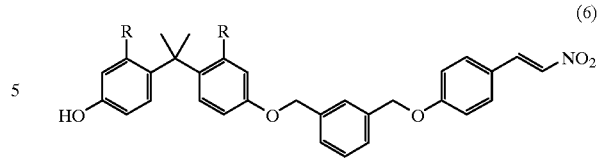

wherein
- PG$_1$ may denote hydrogen or a protecting group suitable for protecting phenols;
- PG may denote a protecting group suitable for protecting amines, where n is 0 or 1 and m may denote the integer 1 or 2;
- Y may denote fluorine, chlorine, bromine or iodine or a C$_{1-4}$-alkyl or an arylsulphonate group, in the presence of an auxiliary base selected from the group comprising alkali or alkaline earth metal hydroxides, alkali or alkaline earth metal carbonates, C$_{1-4}$-alkali metal alkoxides in solvents which are inert under the reaction conditions chosen, such as formamides, preferably dimethylformamide (DMF), C$_{1-4}$-alkylnitriles, preferably acetonitrile, C$_{1-4}$-alkyl esters of carboxylic acids, preferably ethyl acetate or ethyl formate, aromatic or aliphatic hydrocarbons, preferably toluene, or in branched or unbranched C$_{1-4}$-alcohols, and in the following reaction step the protecting groups are cleaved, preferably with inorganic or organic acids in suitable solvents or by hydrogenolysis using methods known from the prior art.

6. Process for preparing compounds of general formula 1, characterised in that a nitrostyrene of general formula 6 is reduced in a solvent selected from the group comprising methanol, ethanol or a higher alcohol, DMF or water in the presence of a catalyst from the group comprising Raney nickel, Pd/C, platinum or with hydride reagents, particularly complex hydrides from the group comprising NaBH$_4$, Ca(BH$_4$)$_2$, LiAlH$_4$ or other aluminium or boron hydrides, at temperatures in the range from 0 to 100° C. and under a hydrogen pressure of more than 760 Torr to yield the corresponding amine of general formula 1.

7. A pharmaceutical comprising a compound of general formula 1 according to claim 1 and the acid addition salts thereof together with conventional excipients and carriers.

8. A method of antagonizing a LTB4 receptor comprising administering to a patient in need of such treatment a pharmaceutically effective amount of a compound according to claim 1.

9. A method of treating a disease selected from the group consisting of arthritis, asthma, chronic obstructive lung diseases, psoriasis, ulcerative colitis, gastropathy or enteropathy induced by nonsteroidal antiinflammatories, cystic fibrosis, Alzheimer's disease, shock, reperfusion damage/ischaemia, atherosclerosis and multiple sclerosis, said method comprising administering to a patient in need of any such treatment a pharmaceutically effective amount of a compound according to claim 1.

10. The method according to claim 8 wherein the chronic obstructive lung disease is chronic bronchitis.

* * * * *